(12) United States Patent
Cross et al.

(10) Patent No.: US 7,931,621 B2
(45) Date of Patent: Apr. 26, 2011

(54) INFUSION ASSEMBLY

(75) Inventors: Brett Cross, Seattle, WA (US); Brett J. Carter, Monroe, WA (US); Nathan Dale, Bothell, WA (US)

(73) Assignee: Calibra Medical, Inc., Redwood City, CA (US)

( * ) Notice: Subject to any disclaimer, the term of this patent is extended or adjusted under 35 U.S.C. 154(b) by 740 days.

(21) Appl. No.: 11/803,007

(22) Filed: May 11, 2007

(65) Prior Publication Data

US 2008/0281270 A1    Nov. 13, 2008

(51) Int. Cl.
*A61M 5/178* (2006.01)
(52) U.S. Cl. ...................................... 604/158
(58) Field of Classification Search .................. 604/122, 604/138, 158
See application file for complete search history.

(56) References Cited

U.S. PATENT DOCUMENTS

| | | | |
|---|---|---|---|
| 5,591,188 | A | 1/1997 | Waisman |
| 5,851,197 | A | 12/1998 | Marano et al. |
| 6,093,172 | A | 7/2000 | Funderburk et al. |
| 6,293,925 | B1 | 9/2001 | Safabash et al. |
| 6,607,509 | B2 | 8/2003 | Bobroff et al. |
| 6,659,982 | B2 | 12/2003 | Douglas et al. |
| 6,673,440 | B2 | 1/2004 | Douglas et al. |
| 6,685,674 | B2 | 2/2004 | Douglas et al. |
| 6,702,779 | B2 | 3/2004 | Connelly et al. |
| 6,830,562 | B2 | 12/2004 | Mogensen et al. |
| 6,923,791 | B2 | 8/2005 | Douglas |
| 6,997,907 | B2 | 2/2006 | Safabash et al. |
| 7,056,302 | B2 | 6/2006 | Douglas |
| 7,318,816 | B2 * | 1/2008 | Bobroff et al. ................ 604/136 |
| 7,648,494 | B2 * | 1/2010 | Kornerup et al. ............. 604/539 |
| 2004/0006316 | A1 | 1/2004 | Patton |
| 2004/0158207 | A1 * | 8/2004 | Hunn et al. .............. 604/164.01 |
| 2005/0107743 | A1 | 5/2005 | Fangrow, Jr. |
| 2005/0124936 | A1 | 6/2005 | Mogensen et al. |
| 2006/0200073 | A1 | 9/2006 | Radmer et al. |
| 2006/0217659 | A1 | 9/2006 | Patton |
| 2007/0123819 | A1 | 5/2007 | Mernoe et al. |

(Continued)

FOREIGN PATENT DOCUMENTS

EP    1 743 667 A2    1/2007

(Continued)

OTHER PUBLICATIONS

Written Opinion for International Appliciation PCT/US2008/006004, Jan. 6, 2009, Korean Intellectual Property Office Daejeon Republic of Korea.
International Search Report for International Application PCT/US2008/006004, Jan. 6, 2009 Korean Intellectual Property Office Daejeon Republic of Korea.

*Primary Examiner* — Nicholas D Lucchesi
*Assistant Examiner* — Diva Ranade
(74) *Attorney, Agent, or Firm* — Richard O. Gray, Jr.; Graybeal Jackson LLP

(57) ABSTRACT

An infusion assembly comprises a cannula subassembly and a source subassembly. The cannula subassembly includes a substantially planar base, a cannula projecting from the base so as to be beneath the patient's skin when the subassembly is deployed, and a generally cylindrical docking structure having a center axis substantially perpendicular to the base. A liquid medicament is dispensed from the cannula. The source subassembly is arranged to dock with the docking structure and includes a supply of liquid medicament that couples to the cannula upon the source subassembly docking with the cannula subassembly. The source subassembly also includes a primer that automatically primes the insulin fluid path to the cannula tip when the subassemblies are joined.

53 Claims, 8 Drawing Sheets

U.S. PATENT DOCUMENTS

| | | |
|---|---|---|
| 2007/0156094 A1 | 7/2007 | Safabash et al. |
| 2007/0282269 A1* | 12/2007 | Carter et al. .............. 604/164.01 |
| 2007/0299408 A1* | 12/2007 | Alferness et al. .............. 604/250 |
| 2008/0119790 A1* | 5/2008 | Hawkins et al. .............. 604/131 |
| 2009/0012472 A1* | 1/2009 | Ahm et al. .................... 604/138 |
| 2009/0043278 A1* | 2/2009 | Tanaka et al. ................. 604/506 |
| 2009/0069750 A1* | 3/2009 | Schraga ................... 604/167.02 |

FOREIGN PATENT DOCUMENTS

| | | |
|---|---|---|
| WO | WO 2006/061354 A1 | 6/2006 |
| WO | WO 2006/077262 A1 | 7/2006 |
| WO | WO 2006/077263 A1 | 7/2006 |
| WO | WO 2006/108809 A1 | 10/2006 |

* cited by examiner

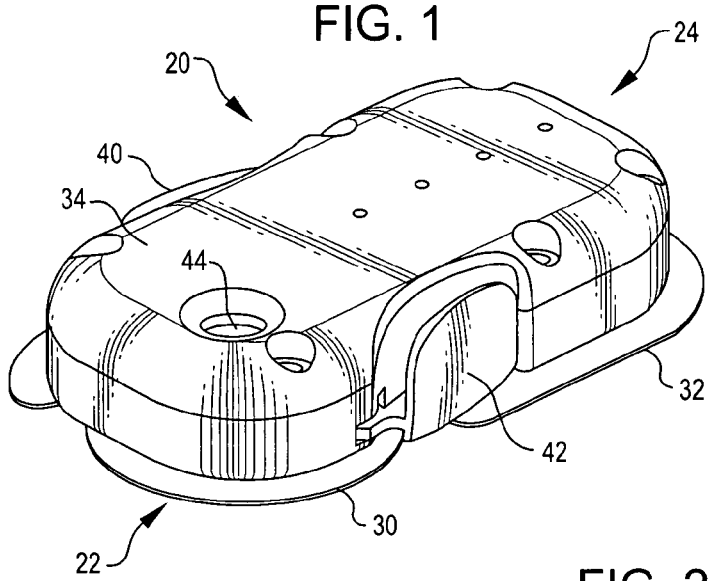
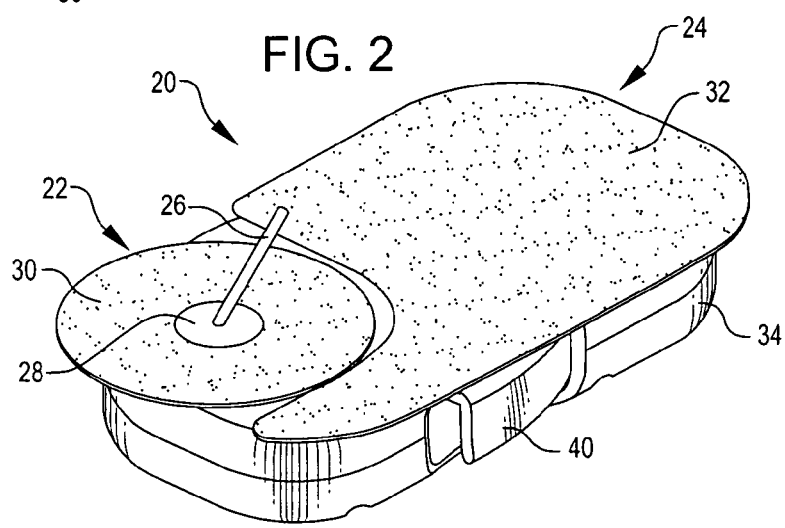
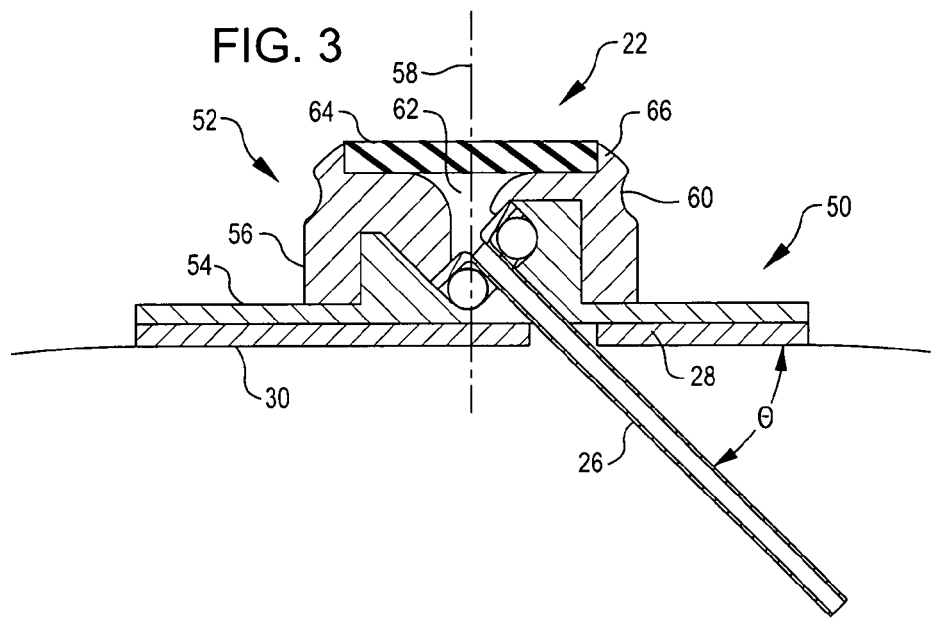

INFUSION ASSEMBLY

BACKGROUND OF THE INVENTION

The present invention relates to an infusion assembly and more particularly to the components of such an assembly and the assemblage thereof that enable liquid medicaments to be delivered to a patient with convenience and in a controlled manner.

Tight control over the delivery of insulin in both type I diabetes (usually juvenile onset) and type II diabetes (usually late adult onset), has been shown to improve the quality of life as well as the general health of these patients. Insulin delivery has been dominated by subcutaneous injections of both long acting insulin to cover the basal needs of the patient and by short acting insulin to compensate for meals and snacks. Recently, the development of electronic, external insulin infusion pumps has allowed the continuous infusion of fast acting insulin for the maintenance of the basal needs as well as the compensatory doses (boluses) for meals and snacks. These infusion systems have shown to improve control of blood glucose levels. However, they suffer the drawbacks of size, cost, and complexity. For example, these pumps are electronically controlled and must be programmed to supply the desired amounts of basal and bolus insulin. This prevents many patients from accepting this technology over the standard subcutaneous injections.

Hence, there is a need in the art for a convenient form of insulin treatment which does not require significant programming or technical skills to implement to service both basal and bolus needs. Preferably, such a treatment would be carried out by an infusion device that is simple to use and mechanically driven negating the need for batteries and the like. It would also be preferable if the infusion device could be directly attached to the body and not require any electronics to program the delivery rates. The insulin is preferably delivered through a small, thin-walled tubing (cannula) through the skin into the subcutaneous tissue similar to technologies in the prior art.

While the idea of such a simple insulin delivery device is compelling, many obstacles must be overcome before such a device may become a practical realty. One problem resides in insulin supply. Patients vary greatly on the amount of insulin such a device must carry to provide treatment over a fixed time period of, for example, three days. This is one environment where one size does not fit all. Another problem is with cannula deployment to support insulin delivery. Cannula deployment to support delivery of the insulin beneath the patient's skin must be made easy and convenient. This is not as easy as it seems because cannula deployment, as generally and currently performed in the art, requires insertion of a cannula carrying needle into the patient and then retraction of only the needle to leave the cannula in place beneath the patient's skin. As will be seen subsequently, the present invention addresses these and other issues toward providing a simple, practical, and reliable insulin delivery device.

SUMMARY OF THE INVENTION

The invention provides a cannula assembly comprising a substantially planar base having a first surface and a second surface, the first surface being opposite the second surface and adapted to adhere to a patient's skin, a cannula projecting from the base first surface so as to be beneath the patient's skin when the assembly is deployed, and a generally cylindrical docking structure having a center axis substantially perpendicular to the base second surface and arranged to receive a source of liquid medicament to be dispensed from the cannula.

The docking structure may include an upper surface having a septum that is arranged to receive a needle extending from the source of liquid medicament. The docking structure may have a locking structure for locking the source of liquid medicament and the docking structure together. Although the locking structure provides a true lock, it may be a releasable locking structure if desired. The docking structure is also preferably arranged to receive the source in any radial orientation.

The locking structure may comprise a detent. The detent may comprise a circumferential groove within the docking structure.

In another embodiment, the invention provides an infusion assembly. The infusion assembly comprises a cannula subassembly and a source subassembly. The cannula subassembly may include a substantially planar base having a first surface and a second surface, the first surface being opposite the second surface and adapted to adhere to a patient's skin, a cannula projecting from the base first surface so as to be beneath the patient's skin when the subassembly is deployed, and a generally cylindrical docking structure having a center axis substantially perpendicular to the base second surface and arranged to receive a source of liquid medicament to be dispensed from the cannula. The source subassembly is arranged to dock with the docking structure and includes a supply of liquid medicament that couples to the cannula upon the source subassembly docking with the cannula subassembly.

The docking structure may include an upper surface having a septum, the source subassembly may include a needle coupled to the supply of liquid medicament and the septum may be arranged to receive the needle of the source subassembly upon the source subassembly docking with the cannula subassembly. The docking structure may have a locking structure for locking to the source subassembly. Also, the docking structure and the source subassembly may be arranged to dock in any radial orientation.

The docking structure may include an upper surface having a septum communicating with the cannula that is arranged to receive the liquid medicament from the supply of liquid medicament and the source subassembly may include a housing having an opening providing an external source of liquid medicament access to the septum. The source subassembly may have a base surface adapted to adhere to the patient's skin and the base surface of the source subassembly may be separate from the cannula subassembly first surface.

The source subassembly may include a needle coupled to the supply of liquid medicament, the cannula may be coupled to the needle of the source subassembly upon the source subassembly docking with the cannula subassembly, and the source subassembly may further include a primer that primes the needle and cannula with the liquid medicament upon the source subassembly docking with the cannula subassembly. The source subassembly may further include a conduit coupling the needle with the supply of liquid medicament. The primer may be within the conduit.

The primer may comprise a collapsible reservoir within the conduit arranged to contain an amount of the liquid medicament. The reservoir may be collapsible upon the source subassembly docking with the cannula subassembly to force the liquid medicament into the needle and cannula. The docking structure may include a septum, and the septum may be arranged to receive the needle of the source subassembly upon the source subassembly docking with the cannula subassembly. The docking structure may be arranged to collapse the reservoir upon the source subassembly docking with the cannula subassembly and the docking structure and the source subassembly may be arranged to permit the septum to receive the needle prior to the docking structure collapsing the reservoir.

In another embodiment, an infusion assembly comprises a cannula subassembly and a source subassembly. The cannula subassembly includes a substantially planar base having a first surface and a second surface, the first surface being opposite the second surface and adapted to adhere to a patient's skin, a cannula projecting from the base first surface so as to be beneath the patient's skin when the subassembly is deployed, and a docking structure arranged to receive a source of liquid medicament to be dispensed from the cannula. The source subassembly is arranged to dock with the docking structure and includes a supply of liquid medicament that couples to the cannula upon the source subassembly docking with the cannula subassembly and a base surface separate from the cannula subassembly first surface and adapted to adhere to the patient's skin.

The docking structure and the source subassembly may be arranged to dock in any radial orientation. The docking structure may include an upper surface having a septum, the source subassembly may include a needle coupled to the supply of liquid medicament and the septum may be arranged to receive the needle of the source subassembly upon the source subassembly docking with the cannula subassembly.

The docking structure may have a locking structure for locking to the source subassembly. Again, the docking structure and the source subassembly may be arranged to dock in any radial orientation.

The docking structure may include an upper surface having a septum communicating with the cannula that is arranged to receive a liquid medicament from an external source of liquid medicament and the source subassembly may include a housing having an opening providing an external source of liquid medicament access to the septum. The base surface of the source subassembly may have a layer of adhesive to adhere the base surface to the patient's skin and the first surface of the cannula subassembly may have a layer of adhesive separate from the base surface layer of adhesive of the source subassembly to adhere the cannula subassembly to the patient's skin independently of the source subassembly.

The source subassembly may include a needle coupled to the supply of liquid medicament, the cannula may be coupled to the needle of the source subassembly upon the source subassembly docking with the cannula subassembly, and the source subassembly may further include a primer that primes the needle and cannula with the liquid medicament upon the source subassembly docking with the cannula subassembly. The source subassembly may further include a conduit coupling the needle with the supply of liquid medicament. The primer may be within the conduit. The primer may comprise a collapsible reservoir within the conduit arranged to contain an amount of the liquid medicament, the reservoir being collapsible upon the source subassembly docking with the cannula subassembly to force the liquid medicament into the needle and cannula. The docking structure may include a septum, and the septum may be arranged to receive the needle of the source subassembly upon the source subassembly docking with the cannula subassembly. The docking structure may be arranged to collapse the reservoir upon the source subassembly docking with the cannula subassembly and the docking structure and the source subassembly may be arranged to permit the septum to receive the needle prior to the docking structure collapsing the reservoir.

In a further embodiment, a cannula assembly comprises a cannula subassembly including a substantially planar base having a first surface and a second surface, the first surface being opposite the second surface and adapted to adhere to a patient's skin, a cannula projecting from the base first surface at a preset angle other than ninety degrees with respect to the patient's skin so as to be beneath the patient's skin when the subassembly is deployed, and a generally cylindrical docking structure having a center axis substantially perpendicular to the base second surface and arranged to receive a source of liquid medicament to be dispensed from the cannula. The assembly further comprises a cannula driver arranged to drive the cannula subassembly base first surface to a deployed position on the skin of the patient along a path defining the preset angle with respect to the patient's skin.

The cannula driver may include a needle carrying the cannula and be arranged to translate the needle and cannula into the deployed position beneath the patient's skin. The cannula driver may include a drive element that drives the cannula subassembly to the deployed position with the base first surface adhered to the patient's skin and the needle and cannula beneath the patient's skin and at the preset angle with respect to the patient's skin. The drive element may include a spring.

The cannula driver may include a needle carrying the cannula. The cannula driver may be arranged to translate the needle and cannula from the cannula driver to the deployed position, and the cannula driver may further be arranged to withdraw the needle from the cannula and return the needle to the cannula driver leaving the cannula in the deployed position projecting from the base first surface beneath the patient's skin. The cannula driver may include an inner compartment and the cannula driver may be arranged to release the needle into the inner compartment after withdrawing the needle from the cannula.

The cannula driver has a distal end that may be arranged to engage the patient's skin and establish the path defining the preset angle with respect to the patient's skin. The cannula driver may include a drive element that withdraws the needle from the cannula and returns the needle to the cannula driver leaving the cannula in the deployed position beneath the patient's skin.

The cannula driver may include an actuator which, when acted upon, causes the cannula assembly to be driven to the deployed position and a lock-out structure that precludes the actuator from being inadvertently acted upon. The lock-out structure may overlie the actuator. The lock-out structure may be a break-away cap structure.

The docking structure may include an upper surface having a septum that is arranged to receive a needle of the source of liquid medicament. The docking structure may further have a locking structure that locks the source of liquid medicament and the docking structure together. The locking structure may include a detent. The detent may comprise a circumferential groove.

The docking structure may have a locking structure for releasably locking the cannula subassembly within the cannula driver. The locking structure may comprise a detent. The detent preferably comprises a circumferential groove within the docking structure.

In another embodiment, an infusion assembly comprises a cannula subassembly including a base, a cannula projecting from the base so as to be beneath the patient's skin when the subassembly is deployed, and a docking structure arranged to receive a source of liquid medicament to be dispensed from the cannula. The assembly further comprises a source subassembly arranged to dock with the docking structure. The source subassembly includes a supply of liquid medicament that couples to the cannula upon the source subassembly docking with the cannula subassembly and a primer that primes the cannula with the liquid medicament upon the source subassembly docking with the cannula subassembly.

The source subassembly may further include a conduit coupling the cannula with the supply of liquid medicament. The primer may be within the conduit.

The primer preferably comprises a collapsible reservoir within the conduit arranged to contain an amount of the liquid medicament. The reservoir is collapsible upon the source subassembly docking with the cannula subassembly to force the liquid medicament into the cannula.

The source subassembly may include a needle coupled to the supply of liquid medicament, and the cannula may be coupled to the needle of the source subassembly upon the source subassembly docking with the cannula subassembly. The primer may then prime the needle and cannula with the liquid medicament upon the source subassembly docking with the cannula subassembly.

The docking structure may include a septum arranged to receive the needle of the source subassembly upon the source subassembly docking with the cannula subassembly. The docking structure and the source subassembly are arranged to permit the septum to receive the needle prior to the docking structure collapsing the reservoir.

In a still further embodiment, a cannula assembly comprises a cannula subassembly including a substantially planar base having a first surface and a second surface, the first surface being opposite the second surface and adapted to adhere to a patient's skin, a cannula projecting from the base first surface at a preset angle other than ninety degrees with respect to the patient's skin so as to be beneath the patient's skin when the subassembly is deployed, and a docking structure projecting from the base second surface and arranged to receive a source of liquid medicament to be dispensed from the cannula. The assembly further comprises a cannula driver arranged to drive the cannula subassembly to a deployed position on the skin of the patient along a path defining the preset angle with respect to the patient's skin. The cannula driver has a stabilizing base to engage the patient's skin and an actuator arranged to be acted upon in a direction substantially transverse to the stabilizing base for actuating the cannula driver.

The docking structure is generally cylindrically shaped and has a center axis substantially transverse to the base second surface. The cannula driver includes a needle carrying the cannula, and the cannula driver is arranged to translate the needle and cannula into the deployed position beneath the patient's skin. The cannula driver includes a drive element that drives the cannula subassembly to the deployed position with the base first surface adhered to the patient's skin and the needle and cannula beneath the patient's skin and at the preset angle with respect to the patient's skin. The drive element may include a spring.

The cannula driver may include a needle carrying the cannula. The cannula driver may be arranged to translate the needle and cannula from the cannula driver to the deployed position, and further arranged to withdraw the needle from the cannula and return the needle to the cannula driver leaving the cannula in the deployed position projecting from the base first surface beneath the patient's skin. The cannula driver may include an inner compartment and the cannula driver may be arranged to release the needle into the inner compartment after withdrawing the needle from the cannula.

The cannula driver may have a distal end arranged to engage the patient's skin and establish the path defining the preset angle with respect to the patient's skin. The cannula driver may include a drive element that withdraws the needle from the cannula and returns the needle to the cannula driver leaving the cannula in the deployed position beneath the patient's skin. The drive element may be a spring.

The cannula driver may include an actuator which, when acted upon, causes the cannula assembly to be driven to the deployed position and a protective cover overlying the actuator that precludes the actuator from being inadvertently acted upon.

The protective cover preferably is a break-away cap structure.

The docking structure may include an upper surface having a septum that is arranged to receive a needle of the source of liquid medicament. The docking structure may further have a locking structure that locks the source of liquid medicament and the docking structure together. The locking structure may be a releasable locking structure comprising a detent. The detent may take the form of a circumferential groove within the docking structure.

The docking structure may have a locking structure for releasably locking the cannula subassembly within the cannula driver. The locking structure may a detent formed by a circumferential groove within the docking structure.

In a still further embodiment, a cannula driver deploys a cannula subassembly in a deployed position on the skin of a patient. The driver comprises a carrier that translates the cannula subassembly along a path defining a preset angle of other than ninety degrees with respect to the patient's skin, a stabilizing base to engage the patient's skin, and an actuator arranged to be acted upon in a direction substantially transverse to the stabilizing base for actuating the cannula driver.

The cannula subassembly includes a base and a cannula projecting from the base at the preset angle. The carrier maintains the cannula base substantially parallel to the stabilizing base as the cannula subassembly is translated for deployment.

The carrier includes a needle that is received by the cannula and carries the cannula subassembly to the deployed position. A drive element acts upon the carrier to drive the cannula subassembly to the deployed position. The drive element may include a spring.

The carrier may include a needle that is received by the cannula and carries the cannula subassembly to the deployed position. The cannula driver may be further arranged to withdraw the needle from the cannula and return the needle to the cannula driver leaving the cannula in the deployed position projecting from the cannula subassembly base beneath the patient's skin. The cannula driver may include an inner compartment and the cannula driver may be arranged to release the needle into the inner compartment after withdrawing the needle from the cannula.

The driver may further include a drive element that withdraws the needle from the cannula and returns the needle to the cannula driver leaving the cannula in the deployed position beneath the patient's skin. The drive element may be a spring.

The cannula driver may include an actuator which, when acted upon, causes the cannula assembly to be driven to the deployed position and a protective cover overlying the actuator that precludes the actuator from being inadvertently acted upon.

The protective cover may be a break-away cap structure.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 1 is a top perspective view of an infusion assembly embodying the present invention;

FIG. 2 is bottom perspective view of the infusion assembly of FIG. 1 embodying the present invention;

FIG. 3 is a cross-sectional side view to an enlarged scale of a cannula subassembly embodying the present invention;

DETAILED DESCRIPTION OF THE INVENTION

Figure 4:
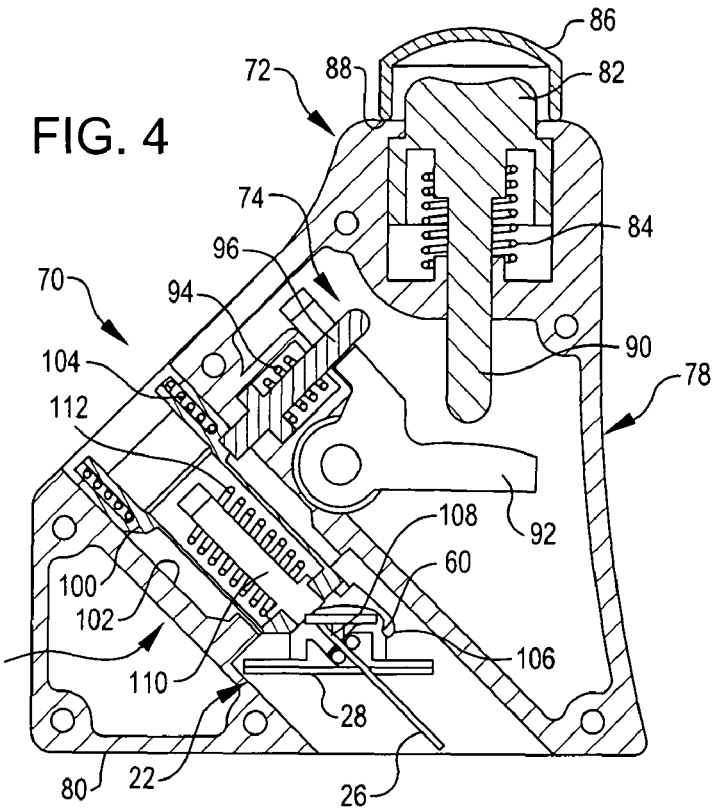
FIG. 4 is a side view, with portions cut away, of a cannula subassembly driver embodying the present invention.

Referring now to FIGS. 1 and 2, they show an infusion assembly 20 embodying the present invention. The infusion assembly is arranged to be worn on the skin of a patient and is preferably disposable after use. To that end, the infusion assembly generally includes a cannula subassembly 22 and a source subassembly 24. The cannula subassembly 22 and source subassembly 24 are initially separate units that may be docked together to form the infusion assembly 20. Each is deployed by the patient separately, first the cannula subassembly 22 and then the source subassembly 24.

As may be noted, the cannula subassembly 22 includes a cannula 26 projecting from a first or bottom surface 28 so that when the cannula subassembly is deployed on the patient's skin, the cannula projects to beneath the skin of the patient. This supports the delivery of liquid medicament, such as insulin, to the patient from the cannula 26. The surface includes an adhesive coated portion 30 to permit the cannula subassembly 22 to adhere to the patient's skin.

The source subassembly 24 similarly includes an adhesive coated bottom surface 32. This permits the source subassembly 24 to adhere to the patient's skin. It is to be particularly noted that, in accordance with one aspect of the present invention, the adhesive coating 30 of the cannula subassembly 22 is separate and independent from the adhesive coating 32 of the source subassembly 24. Hence, each may be independently adhered to the patient's skin.

As may be more readily seen in FIG. 1, the source subassembly 24 includes a pair of actuator buttons 40 and 42. When a bolus of insulin is desired, the buttons are depressed concurrently. If the buttons are not depressed concurrently, the bolus will not be delivered. This prevents accidental actuation of the device. As will be seen subsequently, the source subassembly 24 includes a reservoir that may be filled with the liquid medicament, such as insulin, by the patient before the source subassembly 24 is docked with the cannula subassembly 22. As the source subassembly 24 and cannula subassembly 22 are docked together, the cannula 26 is primed with insulin and a fluid path from the reservoir of the source subassembly to the cannula 26 is established. Concurrent depression of the buttons 40 and 42 then causes the dose of insulin to be pumped from the reservoir to and out of the cannula 26. A bolus may comprise a plurality of such doses.

The source subassembly 24 further includes a port 44 within its housing 34. The port 44 communicates with the cannula 26 as will be seen herein after. This permits injections of insulin or another liquid medicament from a separate external source to be introduced into the port 44 and administered to the patient through the cannula 26.

FIG. 3 is a side view in cross section of the cannula subassembly 22. The cannula subassembly includes a base 50 and a docking structure 52. The base defines the first surface 28 and a second surface 54. The first surface 28 and the second surface 54 are parallel to each other. The docking structure comprises a cylindrical structure 56 having a center axis 58. The center axis extends substantially transverse to the second surface 54. Hence, a source subassembly received on the docking structure 52 in any radial orientation. The docking structure includes a locking structure in the form of a detent 60 and more particularly in the form of a circumferential groove to releasably receive the source subassembly 24. As will be seen subsequently, the source subassembly 24 includes a complementary projection to be received within the groove 60. The groove 60, as will be seen subsequently, also enables the cannula subassembly to be releasably held within a deployment driver as it is translated to a deployed position on the patient.

The docking structure 52 also includes a chamber 62 communicating with the cannula 26. A septum 64 overlies the chamber 62 within a top surface flange 66. The septum may be pierced by a needle carried by the source subassembly to couple the source subassembly reservoir to the cannula when the source subassembly is docked with the docking structure 52. It may also be pierced by the needle of a syringe to administer insulin or other liquid medicament from a separate external source.

FIGS. 4-12 illustrate a driver 70 and its sequential operation for deploying the cannula subassembly 22 according to an embodiment of the invention. The driver 70 includes an actuator 72, a release mechanism 74, and a drive mechanism 76. The forging are housed in a housing 78 that includes a substantial stabilizing surface 80 arranged to contact a patient's skin.

The actuator 72 comprises a button 82 that is loaded by a spring 84. A protective cover 86 overlies the button 84 to form a lock-out structure to prevent accidental actuation of the driver. The cover 86 is breakable along a frangible connection 88 to permit the cover 86 to be readily removed when use of the driver 70 is desired. The button has an extension 90 arranged to engage a pivotal arm 92 of the release mechanism 74. In doing so, the button 82 and its extension 90 are caused to translate in a direction substantially transverse to the stabilizing surface. This provides better control of the driver actuation for the user.

The release mechanism is biased by a spring 94. When the driver is to be actuated, the extension 90 engages the arm 92 and pushes the arm 92 downward. This causes a release pin 96 to be raised and disengaged form the drive mechanism 76.

More specifically, the drive mechanism 76 includes a carrier 100 that moves within a tubular track 102. The carrier is propelled toward the patient's skin buy a first spring 104. The carrier includes a circumferential bead 106 that is releasably received by the circumferential groove 60 of the cannula subassembly 22. The tubular track 102 directs the carrier along a path that defines an angle with respect to the stabilizing surface that is substantially equal to the non-perpendicular angle theta defined by the cannula 26 and the patient's skin. This maintains the first surface 28 of the cannula subassembly substantially parallel to the patient's skin throughout the cannula subassembly deployment.

During the deployment of the cannula subassembly 22, a cannula needle 108 is received by the cannula 26. The needle 108 is carried by a needle holder 110. As will be seen subsequently, when the cannula subassembly 22 has reached its deployed position, the needle holder 110, and hence the needle, are drawn or pushed back into the driver 70 by a second drive spring 112. The needle 108 and holder 110 are then caused to reside within a chamber to enable safe sharps disposal of the needle. Also, since the needle is disengaged from the drive mechanism, reuse of the driver is precluded.

Figure 5:
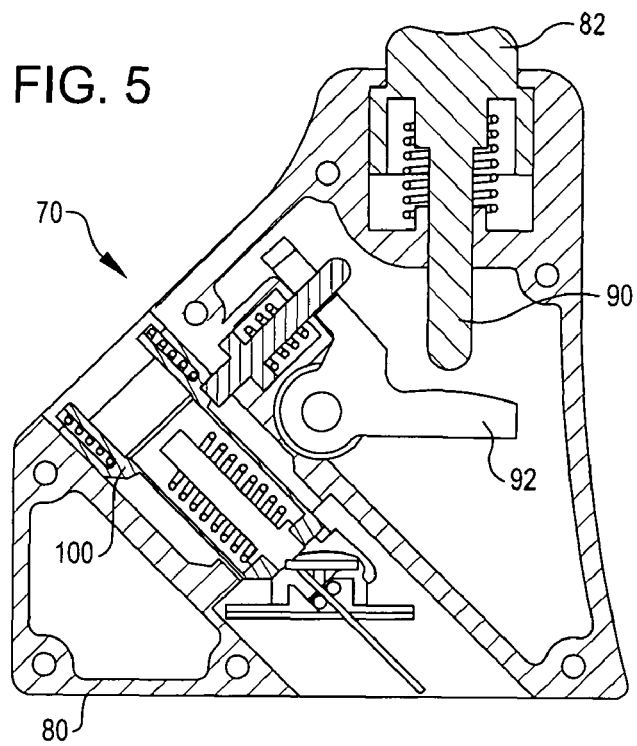
FIG. 5 is side view similar to FIG. 4, with portions cut away, of the cannula subassembly driver of FIG. 4 in an initial pre-actuation stage of driving a cannula subassembly for deployment on and beneath a patient's skin.
Figure 8:
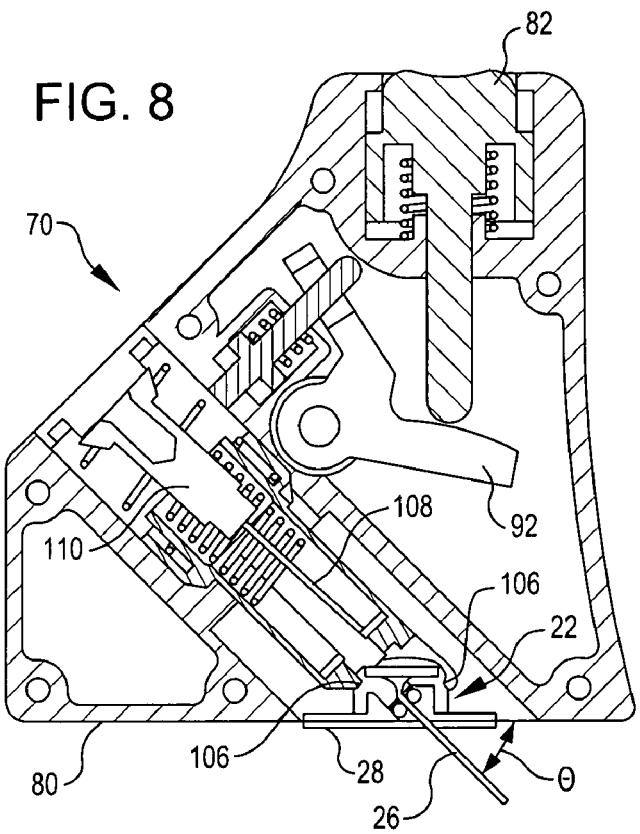
FIG. 8 is another side view, with portions cut away, of the driver of FIG. 4 in a final stage after driving and deploying a cannula subassembly on and beneath a patient's skin in accordance with an embodiment of the present invention.
Figure 9:
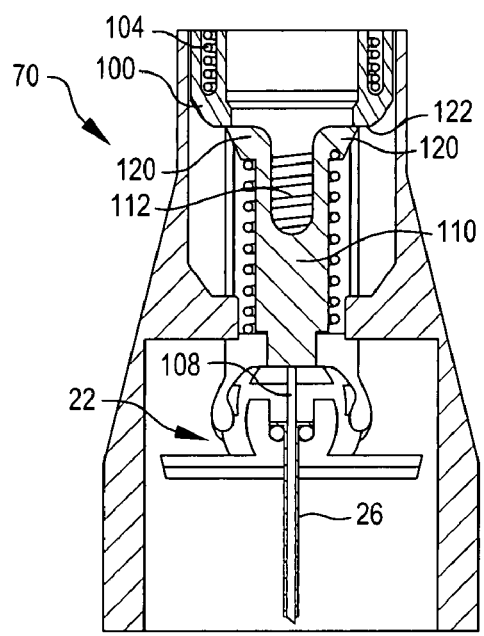
FIG. 9 is a bottom view of the driver of FIG. 4 illustrating the elements thereof in the pre-actuation stage.

FIGS. 5 and 8 show the state of the driver 70 just prior to actuation. In FIG. 5 it will be noted that the protective cover has been removed from the actuator button 82. The needle holder 108 has a pair of legs that abut a circumferential flange 122 of the carrier 100. Hence, when the carrier moves towards the patient's skin, it will push the needle holder 108 and the cannula subassembly 22 together.

Figure 6:
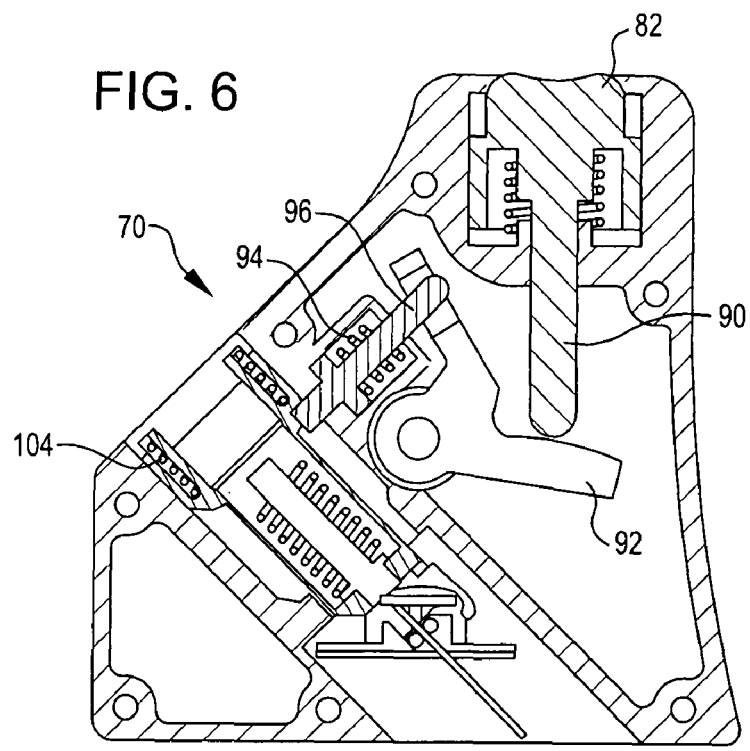
FIG. 6 is another side view, with portions cut away, of the driver of FIG. 4 in a second stage of driving a cannula subassembly for deployment on and beneath a patient's skin in accordance with an embodiment of the present invention.

In FIG. 6 it may be seen that the actuator button 82 has been depressed causing it to engage pivotal arm 92. Arm 92 pivots to raise the release pin 94 against the force of spring 94. The carrier is now free to move towards the patient's skin under the force of the spring 104.

Figure 10:
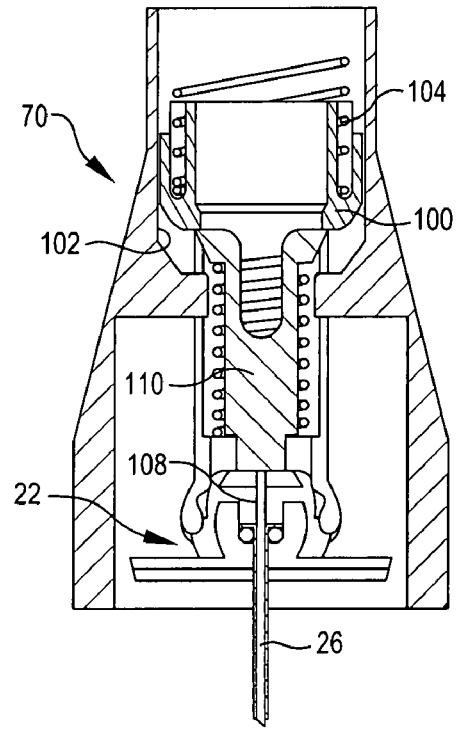
FIG. 10 is a bottom view of the driver of FIG. 4 after the driver has been initially actuated.
Figure 11:
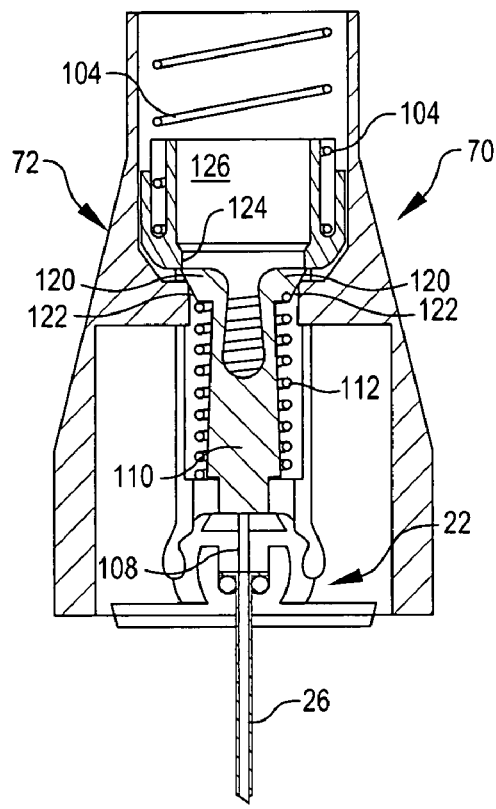
FIG. 11 is a bottom view of the driver of FIG. 4 just prior to the cannula subassembly reaching a fully deployed position.

FIG. 10 shows the carrier 100 on its way towards the patient's skin. It may be noted that the carrier 100 is pushing the needle holder 110. When the carrier 100 begins to reach the end of its travel, the legs 120 of the needle holder engage surfaces 122 of the driver housing 72. These surfaces 122 force the legs 120 inwardly.

Figure 7:
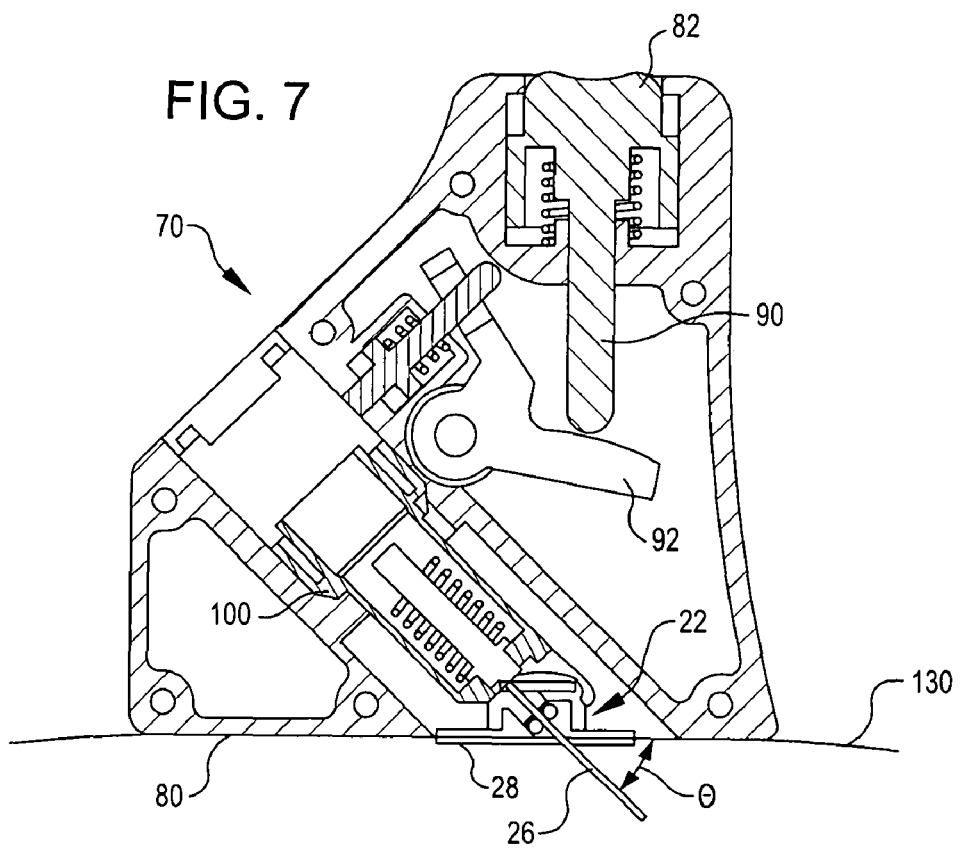
FIG. 7 is another side view, with portions cut away, of the driver of FIG. 4 in a third stage of driving a cannula subassembly for deployment on and beneath a patient's skin in accordance with an embodiment of the present invention.
Figure 12:
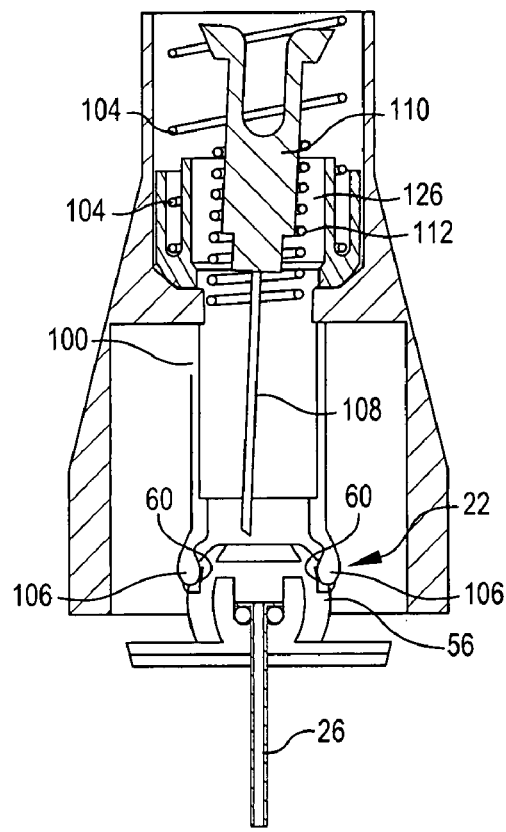
FIG. 12 is a bottom view of the driver of FIG. 4 after the cannula subassembly has been deployed and the cannula needle has been withdrawn from the cannula subassembly back into the driver for safe sharps disposal.

When the carrier has reached the end of its travel as shown in FIG. 7, the cannula subassembly is deployed on the patient's skin 130 and the cannula 26 extends beneath the skin at an angle theta with respect thereto. The legs 120 are now suddenly deflected sufficiently inwardly to clear the inner diameter 124 of the inner chamber 126 of the carrier 100 and the needle holder 110 is pushed by the spring 112 into the chamber 126. The needle 108 and its holder 110 are now free to float within the chamber 126 as shown in FIGS. 8 and 12. The driver may now be removed from the docking structure 56 of the cannula subassembly 22. This may be accomplished by releasing the circumferential bead 106 from the circumferential groove 60 of the docking structure 56 of the cannula subassembly 22.

Figure 13:
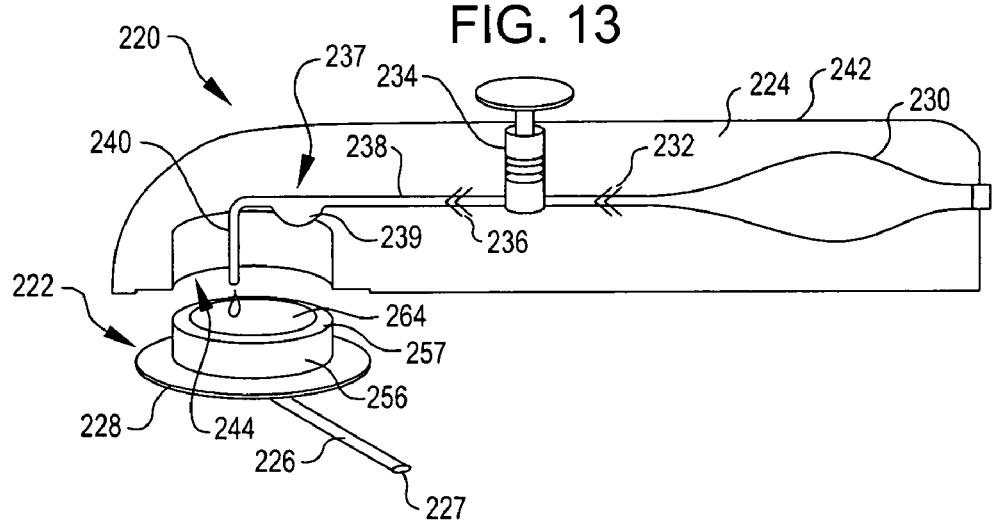
FIG. 13 is a simplified schematic representation of an infusion assembly embodying further aspects of the present invention to illustrate automatic priming thereof.

FIG. 13 is a simplified schematic representation of an infusion assembly 220 embodying further aspects of the present invention. The infusion assembly 220 generally includes a cannula subassembly 222 and a source subassembly 224. The cannula subassembly 222 and source subassembly 224 are initially separate units that may be docked together to form the infusion assembly 220. Each is deployed by the patient separately, first the cannula subassembly 222 and then the source subassembly 224.

The cannula subassembly 222 includes a cannula 226 projecting from a first or bottom surface 228 so that when the cannula subassembly is deployed on the patient's skin, the cannula projects to beneath the skin of the patient. This supports the delivery of liquid medicament, such as insulin, to the patient from the cannula 226. The surface 228 includes an adhesive coating to permit the cannula subassembly 222 to adhere to the patient's skin. As in the previous embodiment, the cannula subassembly 222 includes a cylindrical docking structure 256. The docking structure 256 is covered by a septum 264 and includes a rim surface 257.

The source subassembly includes a reservoir 230, a one-way valve 232, a piston pump 234, another one-way valve 236, a flexible conduit 238, and a needle 240. The source subassembly 224 further includes a housing 242 which has a substantially cylindrical docking port 244 that is dimensioned to receive the docking structure 256 therein. The flexible conduit 238 includes a primer 237. The primer 237 includes a reservoir 239 within the conduit 238 which is filled with the insulin prior to the docking of the source subassembly 224 and the cannula subassembly 222. The reservoir 239 is sized to hold the volume of insulin required to fill the needle 240, the cannula 226, and the conduit between the reservoir 239 and the needle 240 when the cannula subassembly 222 and the source subassembly 224 are brought together. This serves to prime the infusion assembly 220 for eliminating air bubbles from the insulin passageway.

Figure 14:
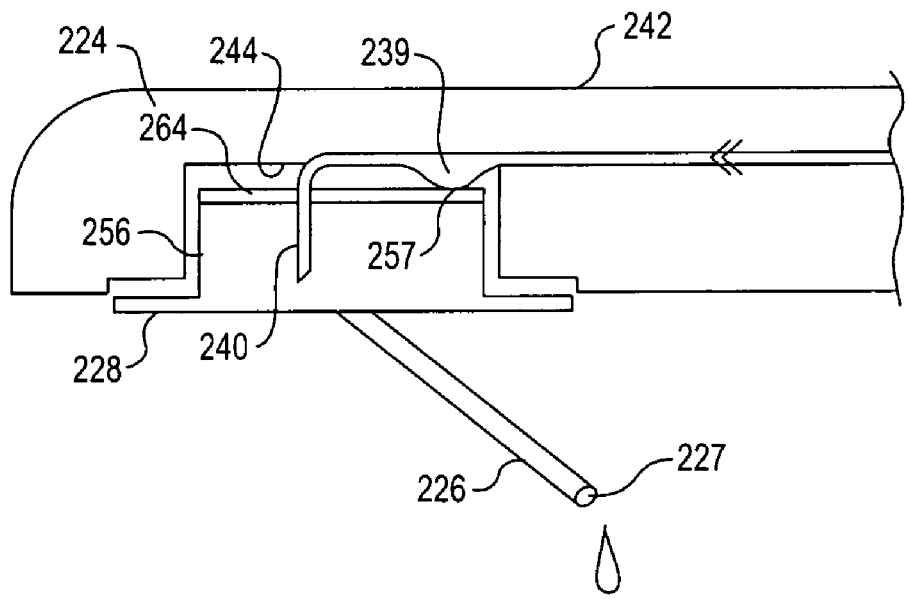
FIG. 14 is a partial view of the source subassembly of FIG. 13 illustrating the priming in process.
Figure 15:
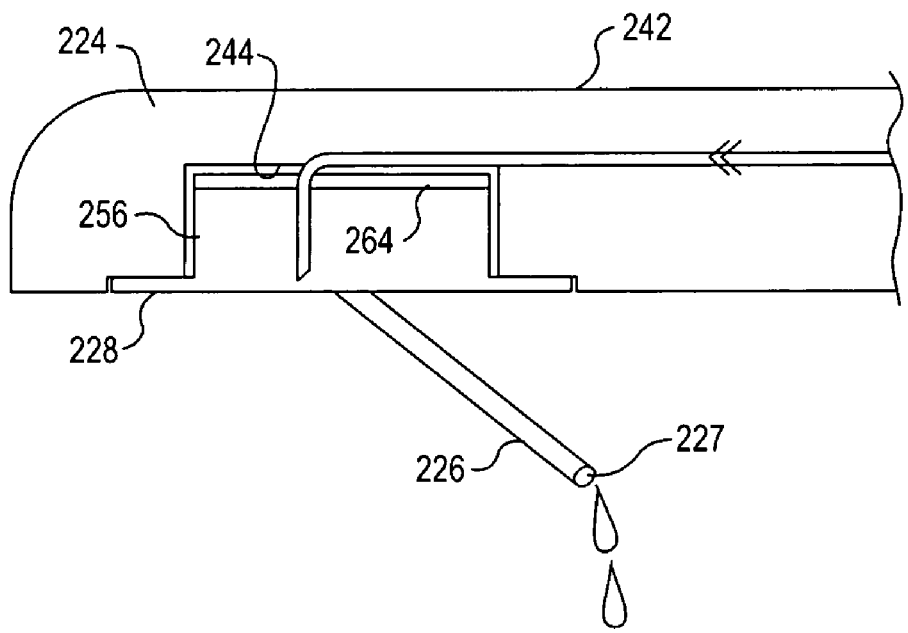
FIG. 15 is a partial view of the source subassembly of FIG. 13 illustrating the completion of the priming process.

More specifically, as may be noted in FIG. 14, as the docking structure 256 of the cannula subassembly 222 is brought into engagement with the docking port 244 of the source subassembly 224, the rim 257 of the docking structure 256 engages the reservoir 239 and collapses it. This forces the insulin therein to flow through the needle 240. Also, as the docking port 244 receives the docking structure 256, the needle 240 penetrates the septum 264 to be in fluid communication with the cannula 226. Hence, during the docking of the cannula subassembly 222 and the source subassembly 224, The flow path to the cannula 226 from the reservoir 230 is established and the flow path to the cannula tip 227 is primed.

Figure 16:
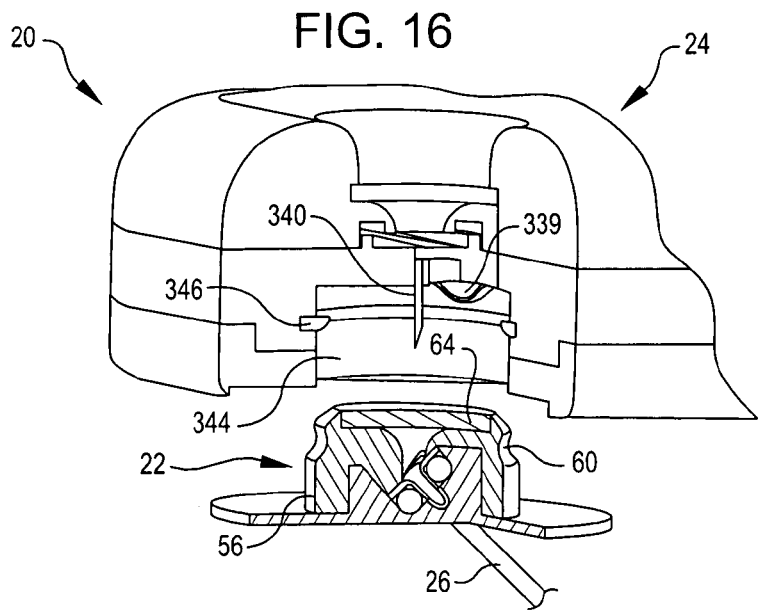
FIG. 16 is a partial perspective view with portions cut away of an infusion assembly embodying the present invention showing a cannula subassembly and a source subassembly prior to docking in accordance with an embodiment of the invention.
Figure 17:
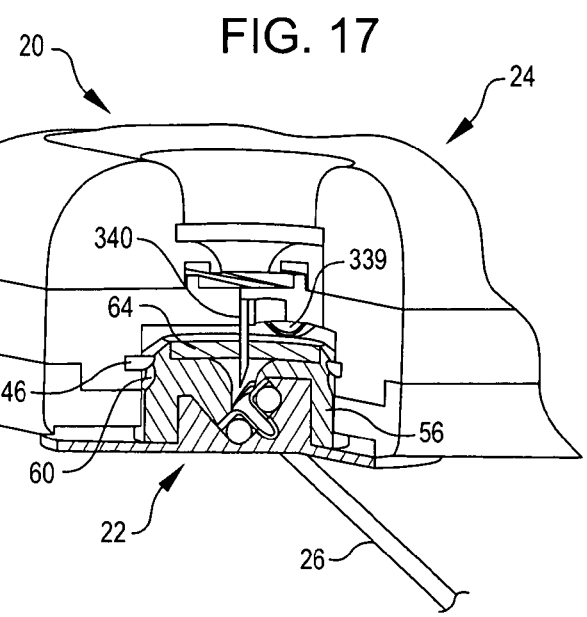
FIG. 17 is a partial perspective view with portions cut away of the cannula subassembly and a source subassembly of FIG. 16 prior to docking according to an embodiment of the invention.
Figure 18:
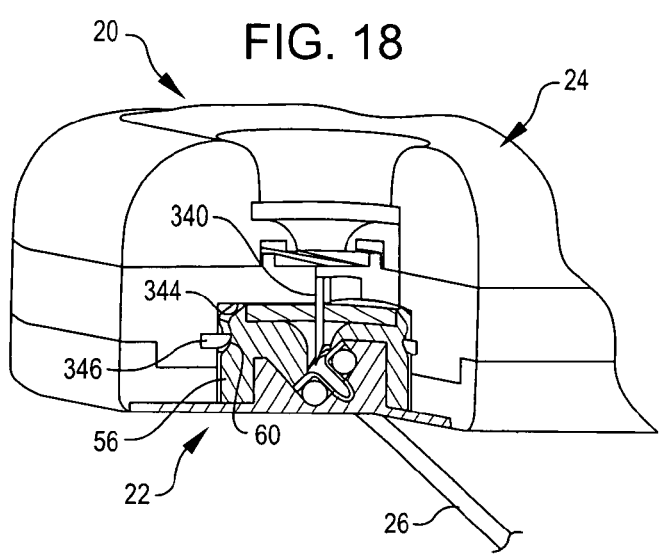
FIG. 18 is a partial perspective view with portions cut away of the cannula subassembly and a source subassembly of FIG. 16 after docking according to an embodiment of the invention.
Figure 19:
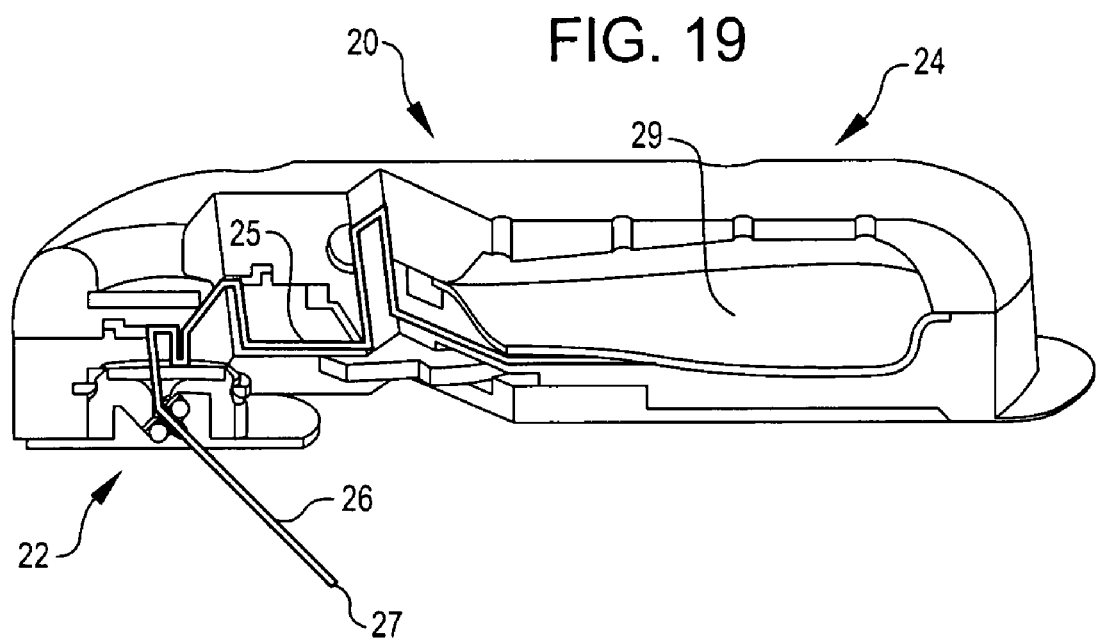
FIG. 19 is a perspective view with portions cut away of the infusion assembly of FIG. 16 showing the liquid medicament flow path established upon the cannula subassembly and source subassembly being docked in accordance with an embodiment of the invention.

FIGS. 16-18, show the docking of the cannula subassembly 22 and the source subassembly 24. As may be seen in FIG. 16, the cannula subassembly 22 is aligned with the substantially cylindrical docking port 344 of the source subassembly 24. As the cannula subassembly 22 enters the docking port 344, the needle 340 of the source subassembly 24 will pierce the septum 64 of the cannula subassembly 22 before the cylindrical docking structure 56 engages the priming reservoir 339. Then, as seen in FIG. 17, the cylindrical docking structure 56 begins to collapse the priming reservoir 339 and the circumferential groove 60 of the cannula subassembly 22 begins to be received by a complimentary circumferential band 346 of within the docking port 344 of the source subassembly 24. Lastly, as may be seen in FIG. 18, when the cylindrical docking structure 56 of the cannula subassembly 22 is fully within the cylindrical docking port 344 of the source subassembly 24, the priming reservoir is fully compressed and the needle 340 has established fluid communication with the cannula 26. Also, the cannula subassembly 22 is locked within the source subassembly 24 by the band 346 having been fully received within the circumferential groove 60. FIG. 19 shows the fluid path 25 established by the cannula subassembly 22 having been fully received in the source subassembly 24 to form the infusion assembly 20. The fluid path extends from the infusion assembly reservoir 29 to the tip 27 of the cannula 22.

While particular embodiments of the present invention have been shown and described, modifications may be made, and it is therefore intended in the appended claims to cover all such changes and modifications which fall within the true spirit and scope of the invention as defined by those claims.

What is claimed is:

1. A cannula assembly comprising:
   a cannula subassembly including a substantially planar base having a first surface and a second surface, the first surface being opposite the second surface and adapted to adhere to a patient's skin, a cannula projecting from the base first surface at a preset angle other than ninety degrees with respect to the patient's skin so as to be beneath the patient's skin when the subassembly is deployed, and a generally cylindrical docking structure having a center axis substantially perpendicular to the base second surface and arranged to receive a source of liquid medicament to be dispensed from the cannula; and
   a cannula driver arranged to drive the cannula subassembly base first surface to a deployed position on the skin of the patient along a path defining the preset angle with respect to the patient's skin.

2. The assembly of claim 1, wherein the cannula driver includes a needle carrying the cannula, and wherein the cannula driver is arranged to translate the needle and cannula into the deployed position beneath the patient's skin.

3. The assembly of claim 2, wherein the cannula driver includes a drive element that drives the cannula subassembly to the deployed position with the base first surface adhered to the patient's skin and the needle and cannula beneath the patient's skin and at the preset angle with respect to the patient's skin.

4. The assembly of claim 3, wherein the drive element includes a spring.

5. The assembly of claim 1, wherein the cannula driver includes a needle carrying the cannula, wherein the cannula driver is arranged to translate the needle and cannula from the cannula driver to the deployed position, and wherein the cannula driver is further arranged to withdraw the needle from the cannula and return the needle to the cannula driver leaving the cannula in the deployed position projecting from the base first surface beneath the patient's skin.

6. The assembly of claim 5, wherein the cannula driver includes an inner compartment and wherein the cannula driver is arranged to release the needle into the inner compartment after withdrawing the needle from the cannula.

7. The assembly of claim 1, wherein the cannula driver has a distal end arranged to engage the patient's skin and establish the path defining the preset angle with respect to the patient's skin.

8. The assembly of claim 7, wherein the cannula driver includes a drive element that withdraws the needle from the cannula and returns the needle to the cannula driver leaving the cannula in the deployed position beneath the patient's skin.

9. The assembly of claim 8, wherein the drive element is a spring.

10. The assembly of claim 1, wherein the cannula driver includes an actuator which, when acted upon, causes the cannula assembly to be driven to the deployed position and a lock-out structure that precludes the actuator from being inadvertently acted upon.

11. The assembly of claim 10, wherein the lock-out structure overlies the actuator.

12. The assembly of claim 11, wherein the lock-out structure is a break-away cap structure.

13. The assembly of claim 1, wherein the docking structure includes an upper surface having a septum that is arranged to receive a needle of the source of liquid medicament.

14. The assembly of claim 1, wherein the docking structure has a locking structure that locks the source of liquid medicament and the docking structure together.

15. The assembly of claim 14, wherein the locking structure is a releasable locking structure.

16. The assembly of claim 14, wherein the locking structure comprises a detent.

17. The assembly of claim 16, wherein the detent comprises a circumferential groove within the docking structure.

18. The assembly of claim 1, wherein the docking structure has a locking structure for releasably locking the cannula subassembly within the cannula driver.

19. The assembly of claim 18, wherein the locking structure comprises a detent.

20. The assembly of claim 19, wherein the detent comprises a circumferential groove within the docking structure.

21. A cannula assembly comprising:
   a cannula subassembly including a substantially planar base having a first surface and a second surface, the first surface being opposite the second surface and adapted to adhere to a patient's skin, a cannula projecting from the base first surface at a preset angle other than ninety degrees with respect to the patient's skin so as to be beneath the patient's skin when the subassembly is deployed, and a docking structure projecting from the base second surface and arranged to receive a source of liquid medicament to be dispensed from the cannula; and
   a cannula driver arranged to drive the cannula subassembly to a deployed position on the skin of the patient along a path defining the preset angle with respect to the patient's skin, the cannula driver having a stabilizing base to engage the patient's skin and an actuator arranged to be acted upon in a direction substantially transverse to the stabilizing base for actuating the cannula driver.

22. The assembly of claim 21, wherein the docking structure is generally cylindrically shaped and has a center axis substantially transverse to the base second surface.

23. The assembly of claim 21, wherein the cannula driver includes a needle carrying the cannula, and wherein the cannula driver is arranged to translate the needle and cannula into the deployed position beneath the patient's skin.

24. The assembly of claim 21, wherein the cannula driver includes a drive element that drives the cannula subassembly to the deployed position with the base first surface adhered to the patient's skin and the needle and cannula beneath the patient's skin and at the preset angle with respect to the patient's skin.

25. The assembly of claim 21, wherein the drive element includes a spring.

26. The assembly of claim 21, wherein the cannula driver includes a needle carrying the cannula, wherein the cannula driver is arranged to translate the needle and cannula from the cannula driver to the deployed position, and wherein the cannula driver is further arranged to withdraw the needle from the cannula and return the needle to the cannula driver leaving the cannula in the deployed position projecting from the base first surface beneath the patient's skin.

27. The assembly of claim 26, wherein the cannula driver includes an inner compartment and wherein the cannula driver is arranged to release the needle into the inner compartment after withdrawing the needle from the cannula.

28. The assembly of claim 21, wherein the cannula driver has a distal end arranged to engage the patient's skin and establish the path defining the preset angle with respect to the patient's skin.

29. The assembly of claim 28, wherein the cannula driver includes a drive element that withdraws the needle from the cannula and returns the needle to the cannula driver leaving the cannula in the deployed position beneath the patient's skin.

30. The assembly of claim 29, wherein the drive element is a spring.

31. The assembly of claim 21, wherein the cannula driver includes an actuator which, when acted upon, causes the cannula assembly to be driven to the deployed position and a protective cover overlying the actuator that precludes the actuator from being inadvertently acted upon.

32. The assembly of claim 31, wherein the protective cover is a cap structure.

33. The assembly of claim 32, wherein the cap structure is a break-away cap structure.

34. The assembly of claim 21, wherein the docking structure includes an upper surface having a septum that is arranged to receive a needle of the source of liquid medicament.

35. The assembly of claim 21, wherein the docking structure has a locking structure that locks the source of liquid medicament and the docking structure together.

36. The assembly of claim 35, wherein the locking structure is a releasable locking structure.

37. The assembly of claim 35, wherein the locking structure comprises a detent.

38. The assembly of claim 37, wherein the detent comprises a circumferential groove within the docking structure.

39. The assembly of claim 21, wherein the docking structure has a locking structure for releasably locking the cannula subassembly within the cannula driver.

40. The assembly of claim 39, wherein the locking structure comprises a detent.

41. The assembly of claim 40, wherein the detent comprises a circumferential groove within the docking structure.

42. A cannula driver that deploys a cannula subassembly in a deployed position on the skin of a patient, comprising:
a carrier that translates the cannula subassembly along a path defining a preset angle of other than ninety degrees with respect to the patient's skin;
a stabilizing base to engage the patient's skin; and
an actuator arranged to be acted upon in a direction substantially transverse to the stabilizing base for actuating the cannula driver.

43. The driver of claim 42, wherein the cannula subassembly includes a base and a cannula projecting from the base at the preset angle and wherein the carrier maintains the cannula base substantially parallel to the stabilizing base as the cannula subassembly is translated for deployment.

44. The driver of claim 42, wherein the carrier includes a needle that is received by the cannula and carries the cannula subassembly to the deployed position.

45. The driver of claim 42, further including a drive element that acts upon the carrier to drive the cannula subassembly to the deployed position.

46. The driver of claim 45, wherein the drive element includes a spring.

47. The driver of claim 42, wherein the carrier includes a needle that is received by the cannula and carries the cannula subassembly to the deployed position and wherein the cannula driver is further arranged to withdraw the needle from the cannula and return the needle to the cannula driver leaving the cannula in the deployed position projecting from the cannula subassembly base beneath the patient's skin.

48. The driver of claim 47, wherein the cannula driver includes an inner compartment and wherein the cannula driver is arranged to release the needle into the inner compartment after withdrawing the needle from the cannula.

49. The driver of claim 47, further including a drive element that withdraws the needle from the cannula and returns the needle to the cannula driver leaving the cannula in the deployed position beneath the patient's skin.

50. The driver of claim 49, wherein the drive element is a spring.

51. The assembly of claim 42, wherein the cannula driver includes an actuator which, when acted upon, causes the cannula assembly to be driven to the deployed position and a protective cover overlying the actuator that precludes the actuator from being inadvertently acted upon.

52. The assembly of claim 51, wherein the protective cover is a cap structure.

53. The assembly of claim 52, wherein the cap structure is a break-away cap structure.

* * * * *